(12) United States Patent
Iori et al.

(10) Patent No.: US 7,014,315 B2
(45) Date of Patent: Mar. 21, 2006

(54) SOFT OPTICAL ELEMENT FOR USE IN EYE-PROTECTING DEVICES

(75) Inventors: Giuseppe Iori, Reggio Emilia (IT); Federico Menta, Parma (IT); Paolo Baiocchi, Parma (IT)

(73) Assignee: Intercast USA, Inc., Plymouth, MA (US)

(*) Notice: Subject to any disclaimer, the term of this patent is extended or adjusted under 35 U.S.C. 154(b) by 113 days.

(21) Appl. No.: 10/821,445

(22) Filed: Apr. 8, 2004

(65) Prior Publication Data

US 2005/0225718 A1    Oct. 13, 2005

(51) Int. Cl.
G02C 7/02    (2006.01)
(52) U.S. Cl. ........................................ 351/159; 351/41
(58) Field of Classification Search .................. 351/41, 351/159
See application file for complete search history.

(56) References Cited

U.S. PATENT DOCUMENTS 4,818,801 A * 4/1989 Rice et al. .................. 526/247

* cited by examiner

Primary Examiner—Scott J. Sugarman
(74) Attorney, Agent, or Firm—Stroock & Stroock & Lavan LLP

(57) ABSTRACT

An optical element is disclosed comprising at least one transparent eye-protecting portion comprising a plastic material, preferably having a hardness within a range of about 40 Shore A to about 77 Shore D, as measured according to ASTM Standard D2240, and an elongation at break within a range of about 200% to about 700%, as measured according to ASTM Standard D638.

19 Claims, 1 Drawing Sheet

U.S. Patent  Mar. 21, 2006  US 7,014,315 B2

SOFT OPTICAL ELEMENT FOR USE IN EYE-PROTECTING DEVICES

FIELD OF THE INVENTION

The present invention relates to an optical element that is suitable for use in eye-protecting devices such as eyeglasses, sunglasses, masks, visors for goggles and helmets, and the like. The eye protecting devices can be, but is not limited to being, ophthalmic. More particularly, the invention relates to an optical element comprising at least one transparent eye-protecting portion comprising a plastic material.

The optical element of the invention may be a semi-finished product from which an ocular for eye-protecting devices, such as a lens for eyeglasses, may be produced by forming and/or beveling the optical element. Alternatively, the optical element of the invention may be a finished product, such as an ocular in the form of lenses for eyeglasses, protection masks or clip-on glasses. The invention also encompasses eye-protecting devices comprising the optical element.

In the following description and in the appended claims, the terms "transparent eye-protecting portion", "eye-protecting device" and "ocular" are intended to indicate elements suitable for protecting the eyes and for allowing adequate vision, as defined by European Standard CEN EN 165 and by US Standard ANSI Z 80.3-1996.

BACKGROUND OF THE INVENTION

When performing outdoor activities, it is common practice to protect the eyes with suitable eye-protecting devices, such as eyeglasses, masks, goggles and the like. These eye-protecting devices can, but need not be, ophthalmic.

Eye-protecting devices are especially an important safety measure when performing outdoor activities such as riding a motorcycle, cycling, running, skiing, sailing, tennis and the like, in order to protect the eyes from sunlight and/or from possible physical impacts.

Sometimes, these eye-protecting devices are worn under a head protecting device, such as a helmet, in activities such as riding a motorcycle, car racing, downhill skiing, climbing, and the like.

In all the abovementioned situations, the eye-protecting devices are often in the form of the so-called "rimless" devices, such as eyeglasses and wrap around eyeglasses, i.e. devices in which the lenses or visors are not surrounded by the frame along their whole periphery, but are attached to a one-piece or multi-piece supporting structure at certain discrete points or outer portions. The "rimless" devices may possess advantageous features by providing a wider view angle and lightness in weight, which are particularly useful when these devices are worn under a helmet.

In a first arrangement of a "rimless" device of this kind, the lens or the visor may be attached to an upper bar of the frame by means of a suitable fixing means, such as screws or rivets. In another rimless arrangement, usually referred to as the "three pieces eyeglass", the eye-protecting device is substantially frameless and the lenses are fixed directly on a central nosepiece and on two temples.

Traditionally, the eye-protecting devices suitable for performing outdoor activities include an optical element comprising at least one transparent portion made of a substantially rigid plastic material having suitable characteristics of low weight, transparency, impact resistance and scratch resistance. Rigid plastic materials used to produce these transparent portions include diethylenglycol-bis-allyl-carbonate or CR39®, polycarbonate, polymethyl methacrylate, cellulose esters, polyurethanes and transparent polyamides. Among them, diethylenglycol-bis-allyl-carbonate or CR39® and polycarbonate are most commonly used for the manufacture of eye-protecting devices suitable for use while performing outdoor activities.

Known optical elements made of these rigid materials, however, have not proven to be entirely satisfactory while in use during outdoor activities, especially when performing outdoor sports activities. For example, the optical elements made of CR39®, while having sufficient impact resistance for use in fashion sunglasses, prove to be unsatisfactory when used in sports sunglasses as, for example, "rimless" and "wrap-around" eyeglasses, since their impact resistance drastically diminishes when they are drilled to form the holes necessary to accommodate the fixing means used to attach the optical elements to the frame. Such holes, in fact, render the optical elements more fragile and brittle in case of impacts. Sometimes, the optical element may even break upon sufficient impact and hurt the eyes or the face of the wearer.

The optical elements made of polycarbonate, on the other hand, while having per se a very good impact resistance, possess such poor scratch and chemical resistance that they require an antiscratch coating, which lowers the impact resistance and enhances the "stress cracking" phenomenon. This phenomenon is provoked by an overload of permanent internal tension that exceeds the elasticity limit, causing the lenses to craze, haze and lose mechanical strength. In addition, the stress cracking phenomenon is worsened when the optical elements made of polycarbonate are drilled to form the holes necessary to accommodate the fixing means in the "rimless" devices and also when the optical element is in contact with materials, such as solvents and greases, or with frames releasing chemicals, such as plasticizers.

These chemicals, furthermore, have a deleterious effect on the haze phenomenon when they are absorbed by the optical elements made of polycarbonate.

With regard to the other transparent rigid materials, such as polyamides, polymethyl methacrylate and cellulose esters, similar problems can arise, since they all have chemical, physical and mechanical characteristics similar to or worse than those of CR39® and polycarbonate.

Finally, all the rigid optical elements currently available are affected by two drawbacks that have not yet been overcome, namely: i) the discomfort the optical elements may cause to the wearer when the eye-protecting device is worn in close contact with the skin under the eyes, a situation which is more and more common with eye-protecting devices suitable for performing outdoor activities, and ii) the discomfort and the possible damage the optical elements may cause if the optical element injures the face of the wearer caused by impact, or worse, if the optical element breaks.

SUMMARY OF THE INVENTION

The primary object of the present invention is to provide an optical element for use in eye-protecting devices, which can, but need not be ophthalmic, which is capable of overcoming at least one of the drawbacks mentioned hereinabove with reference to the prior art.

The optical element of the present invention generally comprises at least one transparent eye-protecting portion comprising a plastic material, preferably having a hardness within a range of about 40 Shore A to about 77 Shore D, as measured according to ASTM Standard D2240, and an elongation at break within a range of about 200% to about 700%, as measured according to ASTM Standard D638.

Another object of the present invention is to provide an optical element for use in eye-protecting devices which is capable of safely protecting the face and the eyes of the wearer in case of an impact with an object during an outdoor activity.

Still another object of the present invention is to provide an optical element for use in eye-protecting devices which is capable of substantially improving the comfort of the wearer of a "rimless" eye-protecting device.

Other objects, features, and characteristics of the present invention will become more apparent upon consideration of the following detailed description with reference to the accompanying drawing, all of which form a part of this specification.

Other objects and features of the present invention will become apparent from the following detailed description, considered in conjunction with the accompanying drawing figure. It is to be understood, however, that the drawing is designed solely for the purpose of illustration and not as a definition of the limits of the invention, for which reference should be made to the appended claims.

BRIEF DESCRIPTION OF THE DRAWINGS

In the drawing figure, which is not to scale, and which is merely illustrative.

DETAILED DESCRIPTION OF THE PREFERRED EMBODIMENTS

Figure 1:
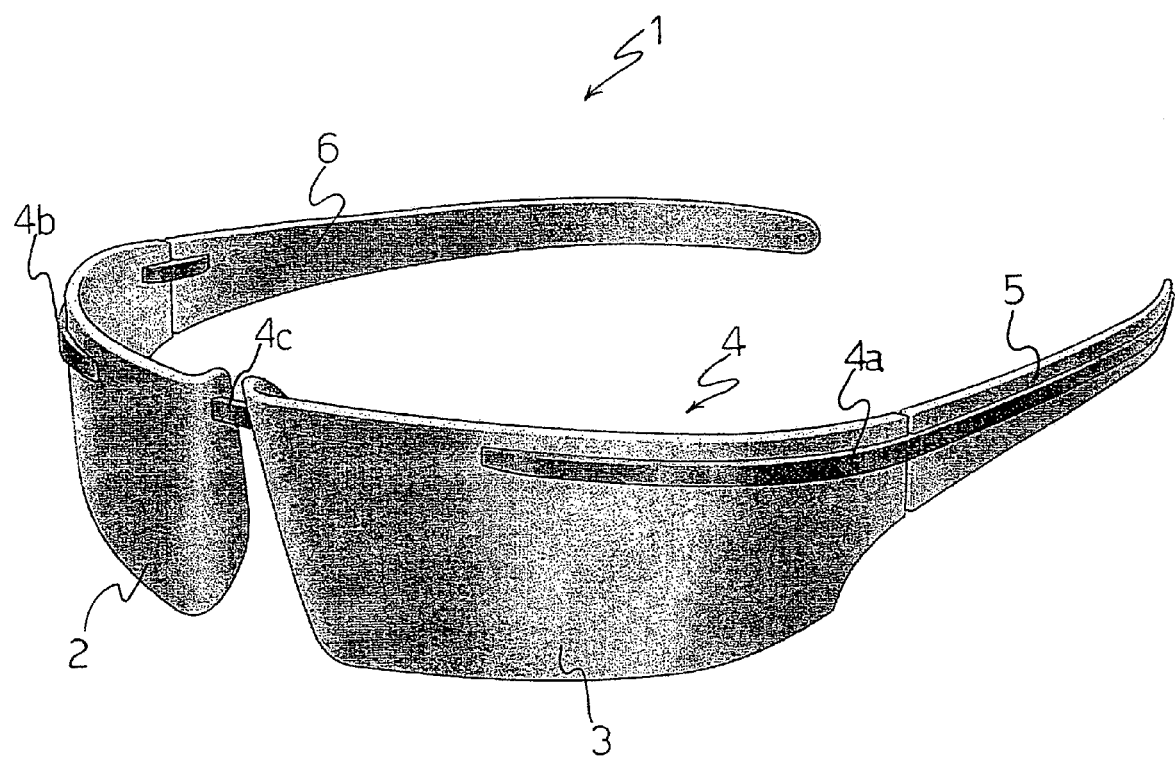
FIG. 1 is a perspective view of eyewear comprising an optical element made in accordance with an embodiment of the invention.

According to the invention, it has been found that the objectives outlined hereinabove may be achieved by an optical element comprising at least one transparent eye-protecting portion comprising a plastic material having an indentation hardness of between about 40 Shore A and 77 Shore D, as measured according to the ASTM Standard D2240, and an elongation at break of between about 200% and about 700%, as measured according to the ASTM Standard D638.

The inventors have found that with a particular combination of specific softness and elasticity characteristics of the eye-protecting transparent portion, the optical element is capable of absorbing the energy of an accidental impact without breaking and maintaining a firm connection to the frame, be it rimless or not, while not causing injury to the face of the wearer.

More specifically, the inventors have found that a suitable softness characteristic may be achieved when the eye-protecting transparent portion of the optical element has a hardness of between about 40 Shore A and 77 Shore D, as measured according to ASTM Standard D2240.

By providing the suitable softness characteristic, the transparent eye-protecting portion may prevent breaking by effectively dissipating a portion of the energy of an accidental impact.

Preferably, the eye-protecting portion comprises a hardness of between about 55 Shore A and 65 Shore D, more preferably, between about 90 Shore A and 60 Shore D, as measured according to ASTM Standard D2240.

As it is known in the art, a durometer instrument can be used to measure surface indentation hardness for the Shore A and Shore D scales, wherein the Shore A scale is softer and the Shore D scale is harder. The upper end of the Shore A scale overlaps with the lower end of the Shore D scale, so as to provide continuity between the two scales. Because this may cause confusion, an abbreviated equivalency chart is given hereinbelow.

100 Shore A~75 Shore D
95 Shore A~50 Shore D
90 Shore A~40 Shore D
85 Shore A~32 Shore D The inventors have also found that suitable elasticity characteristics may be achieved when the eye-protecting transparent portion of the optical element has an elongation at break, defined as the length increase of the specimen at rupture, of between about 200% and about 700% as measured according to ASTM Standard D638.

By providing suitable elasticity, the transparent eye-protecting portion may prevent breaking by effectively absorbing, by bending, a portion of the energy of an accidental impact.

Preferably, the eye-protecting portion has an elongation at break of between about 300% and about 600%, more preferably between about 350% and about 500%, as measured according to ASTM Standard D638.

In a preferred embodiment of the invention, the eye-protecting portion of the optical element has an elongation at yield higher than about 15% as measured according to ASTM Standard D638. The eye-protecting portion therefore is advantageously capable of withstanding extreme bending stresses, such as those applied when the eye-protecting portion is folded in two, without any substantial plastic deformation.

Preferably, the eye-protecting portion of the optical element has an elongation at yield higher than about 50% and, still more preferably, between about 100% and about 300% as measured according to ASTM Standard D638.

The optical element as a whole or at least the transparent eye-protecting portion of the same, should possess adequate optical characteristics so as to render it suitable for its intended purpose.

According to a preferred embodiment, the eye-protecting portion of the optical element has a light transmission not lower than about 85%, more preferably between about 90% and about 93% as measured according to ASTM Standard D1003.

Preferably, the eye-protecting portion has a haze, defined as the percent (%) of incident light not scattered over an angle of 2.5 degrees, that is not higher than 1.5%, more preferably not higher than 1%, most preferably not higher than 0.5%, as measured according to ASTM Standard D1003.

Preferably, the eye-protecting portion has a refractive index lower than about 1.59, more preferably between about 1.52 and about 1.54, as measured according to ASTM Standard D542.

By providing the desired light transmission, haze and refractive index, the vision of objects in the outer environment may be optimized.

In a preferred embodiment of the invention, the optical element includes an eye-protecting portion made of a transparent polyurethane material. Preferably, said polyurethane material is selected from a group comprising polyurea-urethanes, thermoplastic polyurethanes and thermoplastic urea-urethanes.

In one embodiment, the polyurethane material is substantially elastomeric. Transparent elastomeric and non-elastomeric polyurethane materials are particularly effective due to their high transparency, low weight, and chemical resistance. Most importantly, the inventors have found that these preferred polyurethane materials are not subject to any stress cracking phenomenon when drilled to form holes such as for use with rimless devices.

Preferably, the preferred polyurethane materials combine the advantages of materials such as CR39® and polycarbonate without having their drawbacks.

In a preferred embodiment of the invention, the optical element includes an eye-protecting portion made of a transparent plastic material selected from urea-extended thermoplastic elastomeric polyurethanes, such as those disclosed by U.S. Pat. No. 6,258,917.

In another preferred embodiment of the invention, the optical element includes an eye-protecting portion made of a transparent plastic material selected from non-thermoplastic polyurethanes, such as some of the polyurethanes disclosed by U.S. Pat. No. 5,962,617.

Other examples of polyurethane materials which may be used to manufacture the eye-protecting portion of the optical elements of the invention include those that are commercially available from the Bayer Corporation under the trade names of TEXIN® and DESMOPAN®.

These preferred plastic materials can generally be obtained by reacting at least one aliphatic diisocyanate with at least one hydroxy-containing intermediate selected from polyester glycols, polyether glycols, and mixtures thereof, and at least one diamine curing agent.

Optical elements made of polyurethane materials obtained by using aliphatic diisocyanates are preferably substantially free from any yellowing phenomena when exposed to UV rays.

The aliphatic diisocyanates have the basic formula:

wherein A is a straight, branched and/or cyclic aliphatic group having, for example, about 6 to 13 carbon atoms. The aliphatic diisocyanates are preferably saturated diisocyanates.

A preferred aliphatic diisocyanate for use in the process of the present invention is 4,4'-dicyclohexylmethane diisocyanate. An example of such a diisocyanate is DESMODUR® W, a commercially available product of the Bayer Corporation. DESMODUR® W contains 20 percent of the trans, trans isomer of 4,4'-dicyclohexylmethane diisocyanate, with the remaining 80 percent comprising the cis, trans and cis, cis isomers of 4,4'-dicyclohexyl-methane diisocyanate. XP-7041E, also available from the Bayer Corporation, contains 50 percent of the trans, trans isomer of 4,4'-dicyclohexylmethane diisocyanate, with the remaining 50 percent comprising the cis, trans and cis, cis isomers of 4,4'-dicyclohexyl-methane diisocyanate.

Additional diisocyanates that may be used include 3-isocyanato-methyl-3,5,5-trimethylcyclohexyl isocyanate, which is available from Hüls and tetramethylxylene diisocyanate (either meta or para), which is available from Cytex.

The hydroxy-containing intermediates which can be used to prepare the preferred polyurethanes are preferably polyester glycols and polyether glycols having a weight average molecular weight of, for example, about 500 to about 3000.

An example of polyester glycols that can be used to prepare the preferred polyurethanes preferably have a weight average molecular weight of, for example, about 1250 to about 2000 and include polycaprolactones and polyesters based on esterification of aliphatic dicarboxylic acids of 2 to 12 carbon atoms, such as adipic, succinic, and sebacic acids, in the presence of aliphatic glycols having preferably 2 to 12 carbon atoms, such as ethylene glycol, propylene glycol, diethylene glycol, 1,4-butanediol, neopentyl glycol, 1,6-hexanediol, 1,10-decanediol, and 1,12-dodecanediol.

An example of a preferred polyether glycol has a weight average molecular weight of, for example, about 1000 to about 3000 and include poly-1,2-propylene ether glycol, poly-1,3-propylene ether glycol, and polytetramethylene ether glycol (PTMEG). These polyether glycols may be prepared by condensing epoxides or other cyclic ethers according to procedures that are well known in the art.

An example of a preferred hydroxy-containing intermediates for use to prepare the preferred polyurethanes are polycaprolactones, especially the polycaprolactones prepared by the addition reaction of E-caprolactone in the presence of neopentyl glycol, 1,4-butanediol, 1,6-hexanediol, 1,10-decanediol, or 1,12-dodecanediol. The most preferred polycaprolactones are neopentyl glycol-initiated polycaprolactones.

The diamine curing agents, or chain extenders, are preferably primary amines, and more preferably, at least one diamine curing agent is a mixture of two or more diamine curing agents. Examples of diamine curing agents include 2,4-diamino-3,5-diethyl-toluene and 2,6-diamino-3,5-diethyl-toluene, collectively designated as: diethylene toluenediamine (DETDA), methylene dianiline (MDA), and mixtures thereof.

For example, a preferred curing agent is diethylene toluenediamine (DETDA), which is commercially available by the Albemarle Corporation under the trade name ETHACURE® 100. This diamine curing agent is a liquid at room temperature.

Another preferred diamine curing agent that may be used alone or in combination with other diamine curing agents is methylene dianiline (MDA), which is available from Aldrich.

Still another preferred diamine curing agent that may be used alone or in combination with other diamine curing agents may have the following formula:

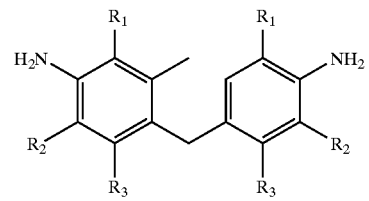

wherein R1 and R2 are each independently selected from methyl, ethyl, propyl, and isopropyl groups, and R3 comprises either hydrogen and chlorine. Examples of these diamine curing agents include the following compounds manufactured by Lonza Ltd. (Basel, Switzerland):
LONZACURE® M-DIPA R1=C3H7; R2=C3H7; R3=H
LONZACURE® M-DMA: R1=CH3; R2=CH3; R3=H
LONZACURE® M-MEA: R1=CH3; R2=C2H5; R3=H
LONZACURE® M-DEA: R1=C2H5; R2=C2H5; R3=H
LONZACURE® M-MIPA: R1=CH3; R2=C3H7; R3=H
LONZACURE® M-CDEA: R1=C2H5; R2=C2H5; R3=Cl
wherein R1, R2 and R3 refer to the above chemical formula. The chemical names of these materials are as follows: M-DIPA is 4,4'-methylene-bis(2,6-diisopropylaniline), M-DMA is 4,4'-methylene-bis(2,6-dimethylaniline), M-MEA is 4,4'-methylene-bis(2-ethyl-6-methylaniline), M-DEA is 4,4'-methylene-bis(2,6- diethylaniline), M-MIPA is 4,4'-methylene-bis(2-isopropyl-6-methylaniline), and M-CDEA is 4,4'-methylene-bis(2,6-diethyl-3-chloroaniline). LONZACURE® M-CDEA is available in the United States from Air Products and Chemicals, Inc. (Allentown, Pa.). Particularly preferred diamine curing agents are M-DIPA (methyl diisopropyl aniline) and M-DEA (methyl diethyl aniline).

A preferred preparation process of the aforementioned polyurethanes comprises the steps of reacting at least one aliphatic diisocyanate with at least one hydroxy-containing intermediate to form a prepolymer, then reacting the prepolymer with at least one diamine curing agent to form a polyurethane.

Alternatively, at least one aliphatic diisocyanate may be reacted with less than one equivalent of the hydroxy-containing intermediate to form a prepolymer, and then the remaining equivalents of the hydroxy-containing intermediate may be added along with at least one diamine curing agent to form a cured polymer.

The optical elements of the present invention may be obtained by casting or injection molding in case of thermoplastic polyurethane elastomers. Casting is a preferred method since it produces optical elements with optimal optical characteristics. In the casting method, the starting materials are poured into an appropriate glass or metal mold and left to cross-link by adopting a suitable time/temperature cycle.

In one embodiment, light-filtering substances adapted to impart the desired spectral characteristics to the optical element or other suitable additives may be incorporated in the aforementioned materials forming the polymer matrix of the optical element. Preferred light-filtering substances which may be incorporated in the aforementioned materials forming the polymer matrix of the optical element include those substances comprising chromophore groups, for instance azobenzene and/or anthraquinone groups as indicated in the Color Index with "Solvent Dyes".

Preferred additives which may be incorporated in the aforementioned materials forming the polymer matrix of the optical element include light stabilizers, UV filters, photochromic dyes and flame retardants.

All these additives are well known and someone of ordinary skill in the art may easily select the most appropriate ones for each specific application among those commercially available.

Preferably, the light-filtering substance or the additives are first incorporated in the optical element, for instance by adding the same to the polymer material, and then by casting or injection molding the latter, to obtain an optical element (such as, for example, a lens or a visor) having a predetermined shape and thickness.

In the alternative, filtering substance or additives can be subsequently added to an optical element molded free from light-filtering substances or additives, for instance, by using well known techniques of transfer, either in the liquid or vapor phase.

In another preferred embodiment of the invention, the optical element may comprise a polarizing film, so as to obtain specific light filtering characteristics.

A preferred preparation process of these optical elements comprises coupling the optical element (such as a lens) with a polarizing film either by inserting the latter into the glass mold during the curing step or by some other coupling system well known in the art.

The optical element of the invention can be in the form of either a semi-finished or a finished product. In one embodiment, the optical element according to the invention may be in the form of a semi-finished product for the manufacture of oculars for eyeglasses.

As described above, the term "ocular" is used herein to indicate an element suitable for allowing vision, such as a lens for eyeglasses, a visor, a protection mask or a clip on optical device, according to the provisions of European Standard CEN EN 165 and U.S. Standard ANSI Z 80.3-1996.

If the optical element in accordance with the invention is a finished product, it may be obtained starting from a respective semi-finished product by means of shaping and possibly beveling operations known per se, or by molding a suitable plastic material.

Preferably, the optical element has a thickness comprised between about 1.0 and about 3.0 mm.

The optical element may be in the form of an ocular in general, such as a soft and flexible lens to be mounted on sunglass frames usable in any sports activity.

As said above, however, the present invention is not limited to lenses for use in sunglass lenses, but may include any type of optical element or eye-protecting device used to protect or shield the eyes of a wearer, such as, for example, lenses for fashion eyewear, sports eyewear, eyeglasses, ophthalmic lenses, visors, shields, face shields, goggles, and the like, as these terms are customarily used in the eyewear industry.

In one embodiment, the optical element may comprise an upper edge, a lower edge, as well as first and second lens portions formed on opposite parts of a groove centrally formed in said lower edge.

The invention also relates to an eye-protecting device comprising an optical element as described hereinabove.

In accordance with one embodiment of the invention, the eye-protecting device is essentially constituted by eyeglasses comprising a supporting frame wherein a couple of lens-shaped oculars are mounted. The lens-shaped oculars may be ophthalmic lenses, i.e. capable of correcting sight defects, or devoid of any corrective capacity.

According to an embodiment, such eye-protecting device may comprise an ocular in the form of a one-piece visor or unitary lens, comprising an upper edge, a lower edge, as well as first and second lens portions, formed on opposite parts of a groove centrally formed in said lower edge.

According to an alternate preferred embodiment, such eye-protecting device is a rimless device as defined above, including devices commonly referred to as "three pieces eyeglass".

As shown in FIG. 1, an eye-protecting device according to a preferred embodiment of the invention can be eyeglasses 1, generally a rimless sports eyeglasses. The eyeglasses 1 comprises two lenses 2, 3 supported by a frame 4.

Lenses 2, 3 comprises at least one eye-protecting transparent portion, which is substantially coincident with lenses 2,3 and is substantially arc-shaped.

Frame 4 comprises two lateral pieces 4a, 4b to which two temples 5, 6 are hingedly attached, and a central piece 4c which connects lenses 2, 3 with one another.

Lenses 2, 3 are preferably made of a polyurethane material and may be obtained by means of conventional casting or injection molding techniques from suitable ingredients such as those described hereinabove.

Additional embodiments of the invention (not shown in the drawing) may include eyeglasses comprising a one-piece optical element, such as a one-piece visor or mask.

In one embodiment, the one-piece mask may comprise an upper edge housed in a corresponding mating groove formed in a frame of suitable shape. The one-piece mask may also comprise a bottom edge as well as first and second lens portions defined on opposite sides with respect to a groove centrally formed in the lower edge, the groove defining a bridge integral with the first and second lens portions.

Some non limiting examples further illustrating optical elements according to the invention will be given by way of indication in the following.

EXAMPLE 1

Twenty lenses having a thickness of about 2 mm and comprising a transparent polyurethane material were obtained by casting using conventional glass molds. More specifically, these lenses were obtained using the following ingredients and procedures.

A clean reactor equipped with heating, cooling, vacuum, dry N2 were provided, and an agitator was charged with DESMODUR® W (4,4'-dicyclohexylmethane diisocyanate containing 20% of the trans, trans isomer). The agitator was turned on and the temperature of the DESMODUR® W was increased to about 71° C.

A mixture comprising polytetramethylene ether glycol (PTMEG) having a weight average molecular weight of about 1000 and polytetramethylene ether glycol (PTMEG) having a weight average molecular weight of about 650, as the hydroxy-containing intermediate, was prepared. The PTMEG mixture was added to the DESMODUR® W in an equivalent ratio of 1.90–2.10 NCO groups to 1.0 OH group.

Heat and vacuum were turned on. When the temperature reached approximately 100° C., the heat was turned off, and the reaction was carried out at a temperature from about 110° to about 121° C. When the reaction was completed and the temperature decreased to approximately 77° C., the resulting prepolymer was discharged from the reactor and filtered through a 200 mesh filter into clean containers. The containers were then purged with dry N2 and were sealed.

The prepolymer was then reacted with diethylene toluenediamine (DETDA), available from the Albemarle Corporation under the trade name ETHACURE® 100 as the diamine curing agent in an equivalent ratio of 0.98–1.0 NH2 groups to 1.0 NCO groups. With the prepolymer at a temperature of approximately 71° C., the ETHACURE® 100 at room temperature was added, and the components were thoroughly mixed. The mixture was then evacuated at about 250 to about 1000 millitorr until it was bubble-free or when only a few bubbles were breaking on the surface. The evacuated mixture was then cast into molds and cured for about 8 to 16 hours at about 105° C.

The lenses obtained were then tested to measure their mechanical and optical characteristics. The results of the tests are shown in Table 1 hereinbelow.

All of the lenses, once mounted on the frame, displayed optimum softness and elasticity characteristics and absorbed, without cracks or damages, the energy imparted by repeated impacts.

EXAMPLE 2

Twenty lenses comprising a transparent polyurethane material were prepared according to the process of Example 1, using polytetramethylene ether glycol (PTMEG) having a weight average molecular weight of about 1000 as the hydroxy-containing intermediate. The PTMEG was added to the DESMODUR® W in an equivalent ratio of 1.45–1.65 NCO groups to 1.0 OH group. The prepolymer was reacted with a 70:30 equivalent mixture of diethylene toluenediamine (DETDA) and methyl diisopropyl aniline (M-DIPA) as the diamine curing agent, which was added to the prepolymer in an equivalent ratio of 0.98–1.0 NH2 groups to 1.0 NCO groups. The cured polymer was cast into a lens having a thickness of about 2 mm.

The lenses were then tested to measure their mechanical and optical characteristics. The results of the tests are shown in Table 1 hereinbelow.

All of the lenses, once mounted on the frame, displayed optimum softness and elasticity characteristics and absorbed, without cracks or damages, the energy imparted by repeated impacts.

EXAMPLE 3

Twenty lenses comprising a transparent polyurethane material were prepared according to the process of Example 1, using E-caprolactone polyesters as hydroxy-containing intermediates.

A mixture comprising diethylene glycol-initiated polycaprolactones, TONE® 0240 (equivalent weight about 1000) and TONE® 0230 (equivalent weight about 625) both available from Dow Chemical, was prepared. A sufficient amount of the TONE® 0230 was added to the TONE® 0240 such that when melted and mixed at about 80° C., an equivalent weight of about 950 was achieved.

The same process as Example 1 was used to prepare the prepolymer, except that the XP-7041E was melted at about 80° C. and thoroughly mixed prior to use.

The E-caprolactone polyesters were added to the diisocyanate (XP-7041E) in an equivalent ratio of about two NCO groups to one OH group.

The curing agent used in this example was diethylene toluenediamine (DETDA). The ratio of NH2 groups to NCO groups was maintained at about 1:1.

The cured polymer was cast into a lens having a thickness of about 2 mm.

The lenses were then tested to measure their mechanical and optical characteristics. The results of the tests are shown in Table 1 hereinbelow.

All of the lenses, once mounted on the frame, displayed optimum softness and elasticity characteristics and absorbed, without cracks or damages, the energy imparted by repeated impacts.

EXAMPLE 4

Twenty lenses comprising a transparent polyurethane material were prepared according to the process of Example 1, using E-caprolactone polyesters as hydroxy-containing intermediates.

A mixture comprising three polycaprolactones, 1,6-hexanediol-initiated polycaprolactone TONE® 32B8 (equivalent weight about 200), 1,6-hexanediol-initiated polycaprolactone TONE® 32C8 (equivalent weight about 375) and 1,4-butanediol-initiated polycaprolactone TONE® 1278 (equivalent weight about 2000), available from Dow Chemical, was prepared. A sufficient amount of the TONE® 32B8 and TONE® 32C8 was added to the TONE® 1278 such that when melted and mixed at about 80° C., an equivalent weight of about 950 was achieved.

The same process as Example 1 was used to prepare the prepolymer.

The E-caprolactone polyesters were added to the diisocyanate (DESMODUR® W) in an equivalent ratio of about 2.5 NCO groups to one OH group.

The curing agent used in this example was diethylene toluenediamine (DETDA). The ratio of NH2 groups to NCO groups was maintained at about 0.98–1.0 NH2 groups to 1.0 NCO groups.

The cured polymer was cast into a lens having a thickness of about 2.2 mm.

The lenses were then tested to measure their mechanical and optical characteristics. The results of the tests are shown in Table 1 hereinbelow.

All of the lenses, once mounted on the frame, displayed optimum softness and elasticity characteristics and absorbed, without cracks or damages, the energy imparted by repeated impacts.

EXAMPLE 5

Twenty lenses having a thickness of about 2.2 mm and comprising the thermoplastic elastomeric polyurethane TEXIN® DP7-3007 by the Bayer Corporation were obtained using conventional injection molding techniques.

The lenses were then tested to measure their mechanical and optical characteristics. The results of the tests are shown in Table 1 hereinbelow.

All of the lenses, once mounted on the frame, displayed optimum softness and elasticity characteristics and absorbed, without cracks or damages, the energy imparted by repeated impacts.

TABLE 1

| Parameter | Test Standard | Ex. 1 | Ex. 2 | Ex. 3 | Ex. 4 | Ex. 5 |
|---|---|---|---|---|---|---|
| Specific Gravity (g/cm$^3$) | ASTM D792 | 1.03 | 1.03 | 1.03 | 1.03 | 1.09 |
| Hardness Shore A/D | ASTM D2240 | 55 (D) | 75 (A) | 85 (A) | 77 (D) | 50 (D) |
| Elongation at Break (%) | ASTM D638 | 480 | 450 | 605 | 220 | 407 |
| Light Transmission (%) | ASTM D1003 | 91 | 91 | 91 | 91 | 91 |
| Haze (%) | ASTM D1003 | 0.32 | <0.5 | <0.5 | <0.5 | <0.5 |
| Refractive Index | ASTM D542 | 1.530 | 1.530 | 1.530 | 1.53 | 1.53 |

While the present invention has been described with reference to one or more embodiments set forth in considerable detail for the purposes of making a complete disclosure of the invention, such embodiments are merely exemplary, and are not intended to limit or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention.

We claim:

1. An optical element comprising at least one transparent eye-protecting portion comprising a plastic material, said eye-protecting portion comprising:
   i) a hardness in a range between about 40 Shore A and about 77 Shore D, as measured according to ASTM Standard D2240; and
   ii) an elongation at break in a range between about 200% and about 700%, as measured according to ASTM Standard D638.

2. The optical element according to claim 1, wherein the hardness is in a range between about 55 Shore A and 65 Shore D, as measured according to ASTM Standard D2240.

3. The optical element according to claim 1, wherein the elongation at break is in a range between about 300% and about 600%, as measured according to ASTM Standard D638.

4. The optical element according to claim 1, wherein the eye-protecting portion comprises an elongation at yield that is higher than about 15%, as measured according to ASTM Standard D638.

5. The optical element according to claim 1, wherein the eye-protecting portion comprises a light transmission not lower than about 85%, as measured according to ASTM Standard D1003.

6. The optical element according to claim 1, wherein the eye-protecting portion comprises a haze not higher than 1.5%, as measured according to ASTM Standard D1003.

7. The optical element according to claim 1, wherein the eye-protecting portion comprises a refractive index lower than about 1.59, as measured according to ASTM Standard D542.

8. The optical element according to claim 1, wherein the eye-protecting portion comprises a polyurethane material.

9. The optical element according to claim 8, wherein said polyurethane material is selected from a group comprising polyurea-urethanes, thermoplastic poliurethanes and thermoplastic urea-urethanes.

10. The optical element according to claim 8, wherein said polyurethane material is substantially elastomeric.

11. The optical element according to claim 9, wherein said polyurethane material is substantially elastomeric.

12. The optical element according to claim 1, wherein the optical element is a semi-finished product suitable for use in the manufacture of oculars for eyeglasses.

13. The optical element according to claim 1, wherein the optical element is an ocular.

14. The optical element according to claim 13, wherein said ocular is a lens for eyeglasses.

15. The optical element according to claim 13, wherein said ocular is a visor.

16. The optical element according to claim 13, wherein said ocular is a protection mask.

17. The optical element according to claim 13, wherein said ocular is a an add-on lens for eyeglasses.

18. An eye-protecting device comprising an optical element according to claim 1.

19. An eye-protecting device according to claim 18, wherein said device is a rimless eyewear.

* * * * *